(12) United States Patent
Brunette

(10) Patent No.: US 7,589,114 B2
(45) Date of Patent: Sep. 15, 2009

(54) DERIVATIVES OF [6,7-DIHYDRO-5H-IMIDAZO[1,2-A]IMIDAZOLE-3-SULFONYL]-AZETIDINE-CARBOXYLIC ACIDS, ESTERS AND AMIDES

(75) Inventor: Steven Richard Brunette, New Milford, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 462 days.

(21) Appl. No.: 11/278,579

(22) Filed: Apr. 4, 2006

(65) Prior Publication Data

US 2006/0229287 A1 Oct. 12, 2006

Related U.S. Application Data

(60) Provisional application No. 60/668,906, filed on Apr. 6, 2005.

(51) Int. Cl.
  *A61K 31/4166* (2006.01)
  *A61K 31/5375* (2006.01)
  *C07D 235/00* (2006.01)
  *C07D 403/12* (2006.01)
(52) U.S. Cl. .............. 514/387; 548/300.1; 548/302.7; 548/303.1; 546/152; 546/168; 546/268.4; 546/273.1; 544/106; 544/139; 544/242; 544/335

(58) Field of Classification Search .............. 548/300.1, 548/301.7, 302.7, 303.1; 514/385, 386, 387; 544/106, 139, 242, 335; 546/152, 168, 268.4, 546/273.1

See application file for complete search history.

(56) References Cited

U.S. PATENT DOCUMENTS

| 6,355,664 | B1 | 3/2002 | Kelly | |
|---|---|---|---|---|
| 6,492,408 | B1 | 12/2002 | Wu | |
| 6,844,360 | B2 | 1/2005 | Kelly | |
| 6,852,748 | B1 | 2/2005 | Kelly | |
| 7,304,067 | B2 * | 12/2007 | Kelly et al. | 514/256 |
| 7,345,074 | B2 * | 3/2008 | Kelly et al. | 514/387 |

FOREIGN PATENT DOCUMENTS

| WO | WO 01/07440 A1 | 2/2001 |
|---|---|---|
| WO | WO 2004/041273 A1 | 5/2004 |
| WO | WO 2004/041827 A2 | 5/2004 |

* cited by examiner

*Primary Examiner*—Golam M Shameem
(74) *Attorney, Agent, or Firm*—Michael P. Morris; Mary-Ellen M. Devlin; Philip I. Datlow

(57) ABSTRACT

Derivatives of 6,7-dihydro-5H-imidazo[1,2-α]imidazole-3-sulfonyl]-azetidine-carboxylic acids, esters and amides which exhibit good inhibitory effect upon the interaction of CAMs and Leukointegrins and are thus useful in the treatment of inflammatory disease.

6 Claims, No Drawings

DERIVATIVES OF [6,7-DIHYDRO-5H-IMIDAZO[1,2-A]IMIDAZOLE-3-SULFONYL]-AZETIDINE-CARBOXYLIC ACIDS, ESTERS AND AMIDES

CROSS-REFERENCE TO RELATED APPLICATIONS

This application claims the benefit of U.S. Provisional Application No. 60/668,906, filed Apr. 6, 2005.

BACKGROUND OF THE INVENTION

1. Technical Field

The present invention relates generally to a series of novel derivatives of [6,7-dihydro-5H-imidazo[1,2-α]imidazole-3-sulfonyl]-azetidine-carboxylic acids, esters and amides, the synthesis of these compounds and their use in the treatment of inflammatory disease.

2. Background Information

Research spanning the last decade has helped to elucidate the molecular events attending cell-cell interactions in the body, especially those events involved in the movement and activation of cells in the immune system. See generally, Springer, T. *Nature,* 1990, 346, 425-434. Cell surface proteins, and especially the Cellular Adhesion Molecules ("CAMs") and "Leukointegrins", including LFA-1, MAC-1 and p150,95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

A group of individuals has been identified which lack the appropriate expression of Leukointegrins, a condition termed "Leukocyte Adhesion Deficiency" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today,* 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1-38, Cosimi, C. B.; et al., *J. Immunol.* 1990, 144, 4604-4612 and Kavanaugh, A.; et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet,* 1989, 2, 1058-1060 and Le Mauff, B.; et al., *Transplantation,* 1991, 52, 291-295).

It has also been demonstrated that a recombinant soluble form of ICAM-1 can act as an inhibitor of the ICAM-1 interaction with LFA-1. Soluble ICAM-1 acts as a direct antagonist of CD18, CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet,* 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the CAMs to the Leukointegrins would make preferable therapeutic agents.

Several small molecules have been described in the literature that affect the interaction of CAMs and Leukointegrins. For example, U.S. Pat. No. 6,355,664 and the corresponding WO 98/39303 disclose a class of small molecule, having a hydantoin core, that are inhibitors of the interaction of LFA-1 and ICAM-1. U.S. Pat. No. 6,492,408 (and corresponding WO 01/07440 A1), U.S. Pat. No. 6,844,360 and U.S. Pat. No. 6,852,748 all discloses compounds having this same activity that instead have a 6,7-dihydro-5H-imidazo[1,2-α]imidazole-3-sulfonyl core.

BRIEF SUMMARY OF THE INVENTION

The invention comprises a class of derivatives of [6,7-dihydro-5H-imidazo[1,2-α]imidazole-3-sulfonyl]-azetidine-carboxylic acids, esters and amides and methods for making the same. These compounds are useful for the treatment of inflammatory conditions in that they exhibit good inhibitory effect upon the interaction of CAMs and Leukointegrins. Thus, the invention further comprises the use of these compounds for the treatment of inflammatory conditions and pharmaceutical compositions comprising the same as active ingredients.

DETAILED DESCRIPTION OF THE INVENTION

In its broadest generic aspect, the invention comprises compounds of the formula I

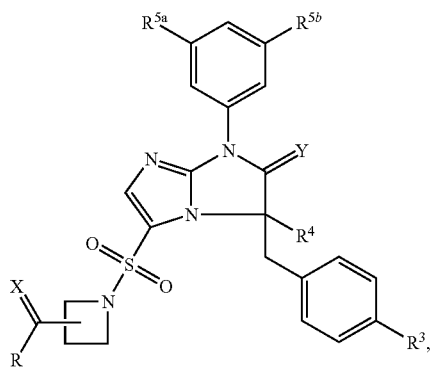

wherein:
R is $OR^1$ or $NR^1R^2$;
$R^1$ and $R^2$ are each, independently selected from the group consisting of:
(A) hydrogen,
(B) —$R^{100}$, which is:
a straight or branched alkyl of 1 to 7 carbon atoms or cycloalkyl of 3 to 6 carbon atoms, which alkyl or cycloalkyl group is mono- or poly substituted with moieties independently selected from the group consisting of:
(i) oxo,
(ii) cyano,
(iii) halogen,
(iv) moieties of the formula —$COOR^6$, wherein $R^6$ is a hydrogen atom, a straight or branched alkyl of 1 to 7 carbon atoms or cycloalkyl of 3 to 6 carbon atoms,
(v) moieties of the formula —$OR^7$, wherein $R^7$ is a hydrogen atom, a straight or branched alkyl group of 1 to 7 carbon atoms or an acyl group of the formula —$COR^8$ wherein $R^8$ is a straight or branched alkyl group of 1 to 7 carbon atoms,
(vi) moieties of the formula —$NR^9R^{10}$, wherein $R^9$ and $R^{10}$ are each, independently selected from the group consisting of:
(a) hydrogen,
(b) straight or branched alkyl of 1 to 7 carbon atoms,
(c) acyl of the formula —$COR^{11}$ wherein $R^{11}$ is a straight or branched alkyl group of 1 to 7 carbon atoms, and
(d) groups of the formula —$COOR^{12}$ wherein $R^{12}$ is a straight or branched alkyl group of 1 to 7 carbon atoms,
or wherein $R^9$ and $R^{10}$ constitute a bridge consisting of 3-5 methylene groups or 2-4 methylene groups and one oxygen atom, such that the groups $R^9$ and $R^{10}$ together with the nitrogen atom between them form a heterocyclic ring,
(vii) saturated, heterocyclic groups, consisting of 3 to 5 methylene groups and one oxygen atom, wherein said heterocyclic groups are optionally mono- or disubstituted with moieties that are independently selected from the group consisting of:
(a) oxo and
(b) straight or branched alkyl of 1 to 3 carbon atoms; and
(viii) aryl or heteroaryl selected from the class consisting of:
(a) phenyl,
(b) pyridyl,
(c) furyl,
(d) tetrazolyl and
(e) thiophenyl;
(C) aryl, selected from the group consisting of:
(i) biphenyl,
(ii) phenyl which is mono- or di-substituted with moieties independently selected from the group consisting of —$NH_2$ and N-morpholino, and
(iii) quinolinyl; and
(D) unsaturated or partially saturated heterocyclic groups consisting of 2 to 3 carbon atoms, 1 to 2 nitrogen atoms, 0 to 1 sulfur atoms and 0 to 1 oxygen atoms wherein said heterocyclic group is optionally mono- or polysubstituted with one or more of the following moieties independently selected from the group consisting of:
(i) oxo and
(ii) straight or branched alkyl of 1 to 7 carbon atoms;
or wherein $R^1$ and $R^2$ constitute a saturated 3 to 5 methylene group bridge which together with the nitrogen atom between them form a heterocyclic ring, wherein one methylene group in the ring may be replaced by O or S, and wherein said heterocyclic ring is mono- or disubstituted with moieties independently selected from the group consisting of:
(A) —OH,
(B) —COOH and
(C) —$COONH_2$;
$R^3$ is:
(A) aryl selected from the group consisting of pyridyl and pyrimidyl, wherein one or more hydrogen atoms of said aryl group are optionally and independently substituted with moieties selected from the group consisting of:
(i) cyano,
(ii) halogen and
(iii) groups of the formula —$NR^{13}R^{14}$, wherein $R^{13}$ and $R^{14}$ are each, independently, hydrogen or straight or branched alkyl of 1 to 3 carbon atoms;
(B) trifluoromethoxy or,
(C) cyano;
$R^4$ is straight or branched alkyl of 1 to 3 carbon atoms;
$R^{5a}$ is Cl or $CF_3$;
$R^{5b}$ is Cl or $CF_3$;
X is an oxygen or a sulfur atom; and
Y is an oxygen or a sulfur atom.
In another embodiment, the invention comprises compounds of the formula I, wherein:
R is $OR^1$ or $NR^1R^2$ $R^1$ and $R^2$ are each, independently selected from the group consisting of:
(A) hydrogen; or
(B) —$R^{100}$, which is:
a straight or branched alkyl of 1 to 4 carbon atoms, which alkyl group is mono- or disubstituted with moieties independently selected from the group consisting of:
(i) oxo,
(ii) OH,
(iii) moieties of the formula —$NR^9R^{10}$, wherein $R^9$ and $R^{10}$ are each, independently selected from a group consisting of:
(a) hydrogen and
(b) methyl,
(iv) tetrazole,
or wherein $R^1$ and $R^2$ constitute a saturated 5 methylene group bridge which together with the nitrogen atom between them form a heterocyclic ring, wherein said heterocyclic ring is monosubstituted with COOH;
$R^3$ is:
(A) aryl selected from the group consisting of 3-pyridyl and 5-pyrimidyl wherein said aryl group is monosubstituted with:
(i) cyano or
(ii) $NH_2$,
(B) trifluoromethoxy or
(C) cyano;
$R^4$ is a methyl group;
$R^{5a}$ is Cl;
$R^{5b}$ is Cl;
X is an oxygen atom and
Y is an oxygen atom.

In yet another embodiment, the invention comprises compounds of the formula I wherein:
R is $OR^1$ or $NR^1R^2$
$R^1$ and $R^2$ are each, independently selected from the group consisting of:
(A) hydrogen, or
(B) —$R^{100}$, which is:
straight or branched alkyl of 1 to 4 carbon atoms, which alkyl group is mono- or disubstituted with moieties independently selected from the group consisting of:
(i) oxo,
(ii) OH and
(iii) $NH_2$;
$R^3$ is trifluoromethoxy or cyano;
$R^4$ is a methyl group;
$R^{5a}$ is Cl;
$R^{5b}$ is Cl;
X is an oxygen atom; and
Y is an oxygen atom.

It will be appreciated that the compounds of the formula I have at least one chiral center. In an ultimately preferred generic aspect, the invention includes compounds of formula I with the absolute stereochemistry depicted below in formula I*.

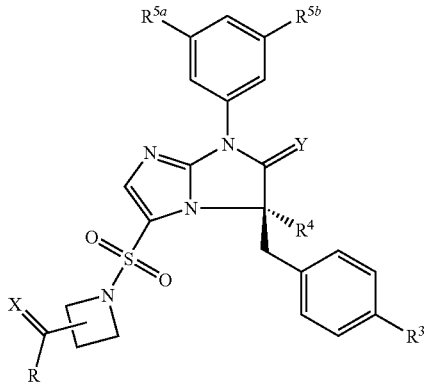

(I*)

In another embodiment, compounds of Formula I include the following:
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methyl ester.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid.
1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methyl ester.
1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid.
1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid isopropyl ester.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropyl ester.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropylamide.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methylamide.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid dimethylamide.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid benzylamide.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(3-picoyl)-amide.
(R)-1-(3,5-Dichloro-phenyl)-3-methyl-5-[(S)-2-(morpholine-4-carbonyl)-azetidine-1-sulfonyl]-3-(4-pyrimidin-5-yl-benzyl)-1H-imidazo[1,2-α]imidazol-2-one.
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(2-hydroxy-ethyl)-amide.

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid((S)-2-hydroxy-1-methyl-ethyl)-amide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methylamide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid dimethylamide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid isopropylamide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid benzylamide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid(3-picoyl)-amide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic (2-hydroxy-ethyl)-amide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic ((S)-2-hydroxy-1-methyl-ethyl)-amide.

(R)-1-(3,5-Dichloro-phenyl)-3-methyl-5-[3-(morpholine-4-carbonyl)-azetidine-1-sulfonyl]-3-(4-pyrimidin-5-yl-benzyl)-1H-imidazo[1,2-α]imidazol-2-one.

(S)-1-[(R)-7-(3,5-Dichloro-phenyl)-5-methyl-6-oxo-5-(4-pyrimidin-5-yl-benzyl)-6,7-dihydro-5H-imidazo[1,2-α] imidazole-3-sulfonyl]-azetidine-2-carboxylic acid amide.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid amide.

(S)-1-[(R)-5-(4-cyano-benzyl)-7-(3,5-dichloro-phenyl)-5-methyl-6-oxo-6,7-dihydro-5H-imidazo[1,2-α]imidazole-3-sulfonyl]-azetidine-2-carboxylic acid amide (S)-1-[(R)-7-(3,5-dichloro-phenyl)-5-methyl-6-oxo-5-(4-trifluoromethoxy-benzyl)-6,7-dihydro-5H-imidazo[1,2-α] imidazole-3-sulfonyl]-azetidine-2-carboxylic acid amide.

(S)-1-[(R)-5-[4-(4-Cyano-pyrimidin-5-yl)-benzyl]-7-(3,5-dichloro-phenyl)-5-methyl-6-oxo-6,7-dihydro-5H-imidazo[1,2-α]imidazole-3-sulfonyl]-azetidine-2-carboxylic acid amide.

The invention also includes pharmaceutically acceptable salts of the compounds of the formula I.

Specific compounds of the present invention may be identified in the present specification by chemical name and/or chemical structure. In the event of any conflict between the chemical name and chemical structure, the chemical structure will control.

In general, all tautomeric and isomeric forms and mixtures thereof, for example, the individual geometric isomers, stereoisomers, enantiomers, diastereomers, racemates, racemic or non-racemic mixtures of stereoisomers, mixtures of diastereomers, or mixtures of any of the foregoing, of a depicted chemical structure or compound is intended, unless the specific stereochemistry or isomeric form is specifically indicated in the compound name or structure.

General Synthetic Methods

Compounds of the invention may be prepared by the general methods described below. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art using methods described in the chemical literature.

Compounds of formula I may be prepared from intermediate II. The synthesis of intermediate II is reported by Wu et al., U.S. Pat. No. 6,492,408, Frutos et al., U.S. Pat. No. 6,414,161, Kelly et al., U.S. Pat. No. 6,844,360, and Wang et al., U.S. Patent Application Publication No. 2006/0025447 A1, all incorporated herein by reference.

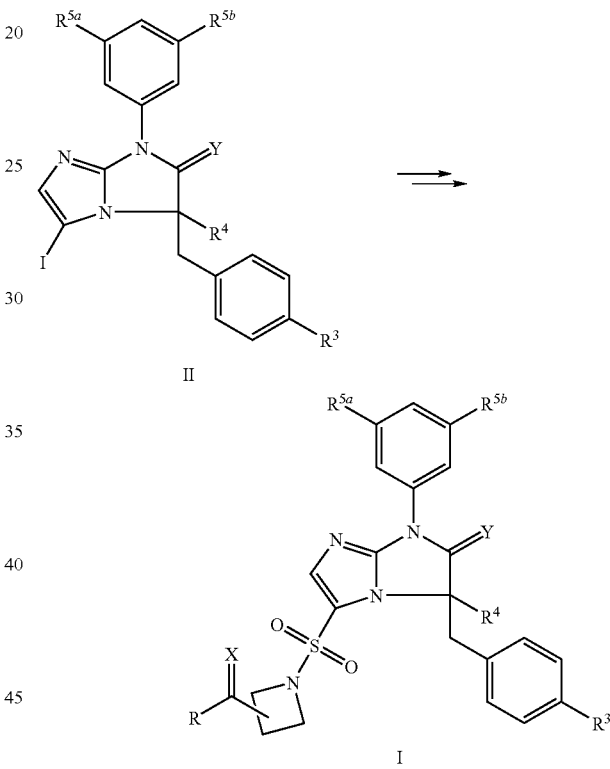

Intermediate II may be prepared by the procedure illustrated in Scheme I.

Scheme I

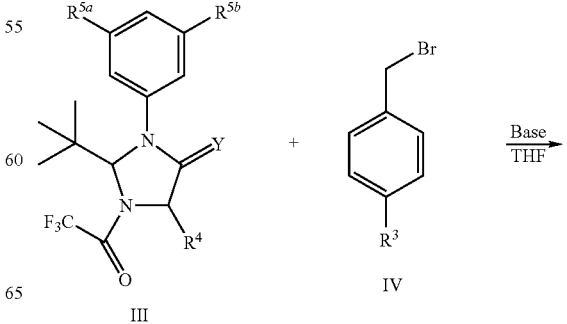

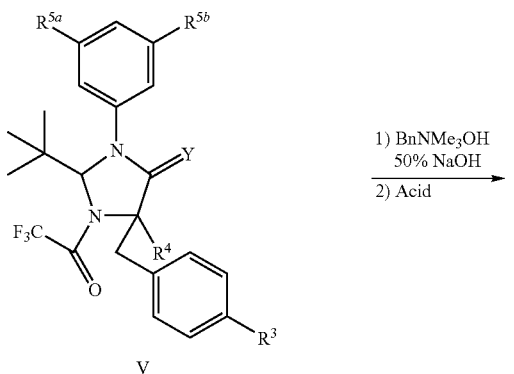

V

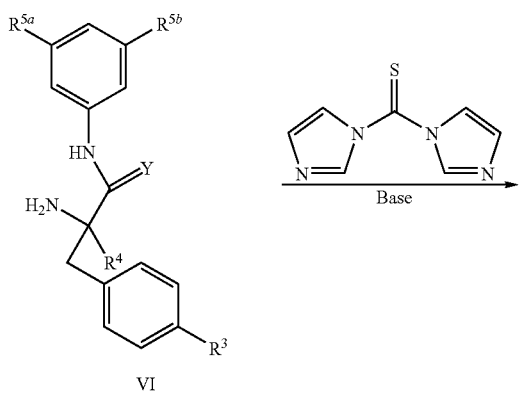

VI

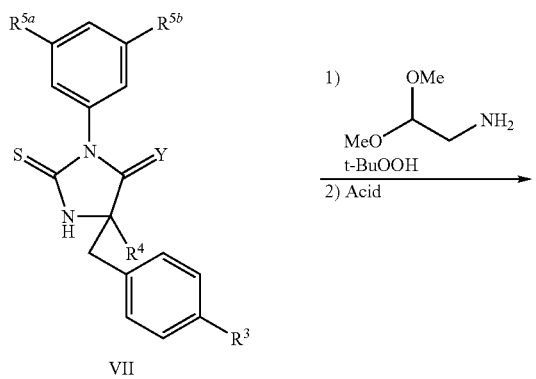

VII

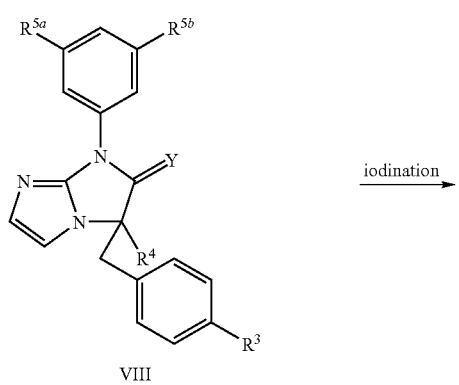

VIII

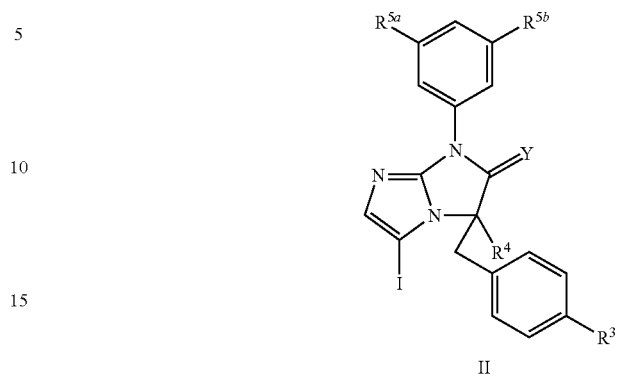

II

As illustrated above, intermediate III is deprotonated with a suitable base such as lithium bis(trimethylsilyl)amide at about −20° C. to −30° C., and then alkylated with a substituted benzyl halide, preferably a benzyl bromide (IV) to produce V. Hydrolysis of the trifluoroacetamide group of V, for example by treatment with 40% aqueous benzyltrimethylammonium hydroxide in dioxane/50% NaOH, followed by treatment with acid, such as HCl, provides VI. Treatment of VI with thiocarbonyldiimidazole in the presence of a base such as 4-(N,N-dimethylamino)pyridine (DMAP) provides VII. Treatment of VII with aminoacetaldehyde dimethyacetal and t-butylhydroperoxide solution, followed by treatment of the intermediate acetal with an acid such as p-toluenesulfonic acid provides VIII. Iodination of VIII by treatment with an iodinating agent such as N-iodosuccinimide provides II.

The method used for preparation of intermediate III, treatment of the amide formed from N-Boc-D-alanine and 3,5-dichloroaniline with trifluoroacetic acid to remove the Boc-group, followed by treatment with pivalaldehyde, and acylation of the resulting imidazolodone with trifluoroacetic anhydride is described in U.S. Pat. No. 6,414,161, cited above, and in the chemical literature (N. Yee, Org Lett., 2000, 2, 2781).

The synthesis of compounds of formula I from intermediate II is illustrated in Scheme II.

Scheme II

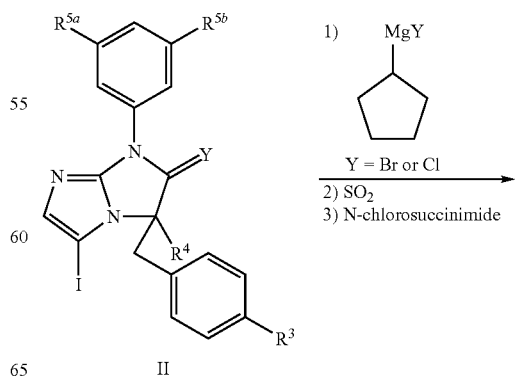

II

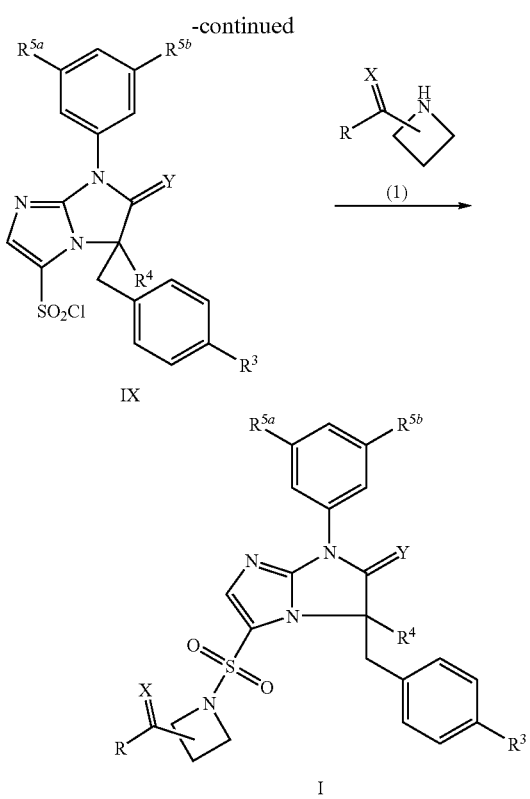

As illustrated above, treatment of II with a Grignard reagent, such as cyclopentyl magnesium bromide or chloride, followed by treatment of the resulting magnesium salt with SO₂ and then N-chlorosuccinimide provides the sulfonyl chloride IX. Treatment of IX with the desired amine (1) in the presence of a suitable base such as triethylamine, provides the desired product of formula (I). Intermediates (1) are either commercially available or readily prepared from commercially available starting materials by methods known in the art. The initial product of formula I may be further modified by methods known in the art to provide additional compounds of the invention. Several examples are provided in the Synthetic Examples section.

The desired $R^3$ on formula I compounds may be obtained by selection of the appropriately substituted intermediate IV in Scheme I. Alternately, intermediate VIII having $R^3$ being Br (VIIIa) may be converted to intermediates having $R^3$ being CN or an optionally substituted 5-pyrimidyl group as illustrated in Scheme III.

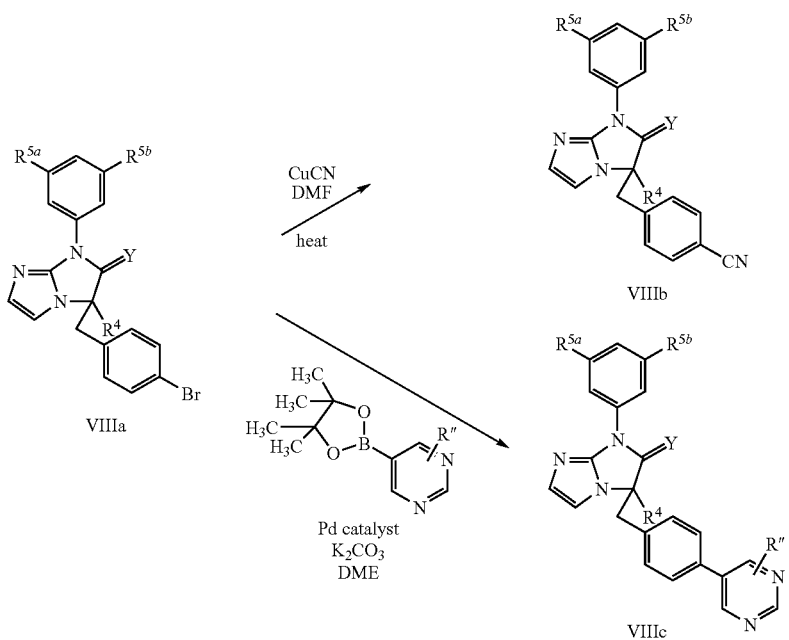

As illustrated above, the aryl bromide VIIIa is treated with a cyanide salt, preferably CuCN and heated in a suitable solvent such as DMF to provide the cyano-intermediate VIIIb. Treatment of VIIIa with a pyrimidine boronate ester such as 5-(4,4,5,5,-tetramethyl-[1,3,2]dioxaborolan-2-yl)-pyrimidine in the presence of a palladium catalyst such as [1,1'-bis(diphenylphosphino)ferrocene]dichloropalladium (II).$CH_2Cl_2$ ($PdCl_2$(dppf).$CH_2Cl_2$) and a base such as potassium carbonate in a suitable solvent (Suzuki reaction), for example dimethoxyethane, provides the pyrimidine intermediate VIIIc. Intermediates VIIIb and VIIIc may then be converted to desired compounds of formula I by the procedures described in Schemes I and II. The Suzuki reaction to convert $R_3$=Br to $R_3$=an optionally substituted pyrimidine may also be carried out on a compound of formula I.

The invention is further described by the following synthetic examples.

SYNTHETIC EXAMPLES

Example 1

Synthesis of (S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid

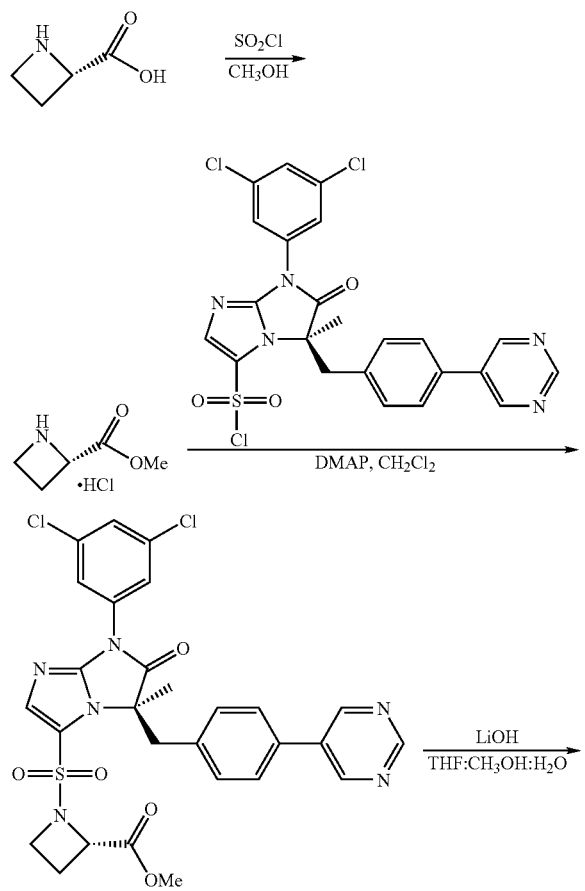

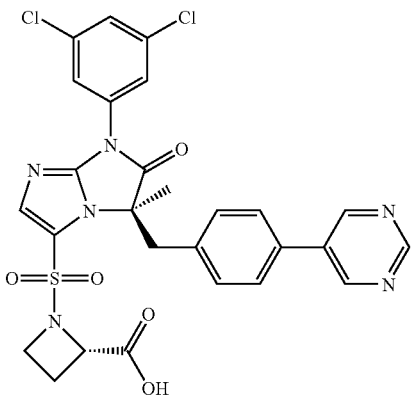

1

Thionyl chloride (0.144 mL) was added to a solution of (S)-(−)-2-azetidinecarboxylic acid (0.1 g, 0.99 mmol) in $CH_3OH$ (4 mL) and stirred at room temperature for 3 h. The volatiles were removed in vacuo to afford 0.180 g of the desired (s)-(−)-azetidine carboxylic acid methyl ester hydrochloride, which was used without further purification.

The above methyl ester hydrochloride (0.056 g, 0.37 mmol) in $CH_2Cl_2$ (1.0 mL) was added to a solution of (S)-1-[(R)-7-(3,5-dichloro-phenyl)-5-methyl-6-oxo-5-(4-pyrimidin-5-yl-benzyl)-6,7-dihydro-5H-imidazo[1,2-α]imidazole-3-sulfonyl chloride (0.170 g, 0.31 mmol) in $CH_2Cl_2$ (5 mL). DMAP (0.114 g) was added and the reaction was stirred for 3 h. The reaction was diluted with $CH_2Cl_2$ and poured into saturated aqueous $NH_4Cl$. The aqueous phase was separated and extracted twice with $CH_2Cl_2$. The organic layers were combined, dried over anhydrous $Na_2SO_4$, decanted and concentrated in vacuo. The resultant residue was purified by silica gel chromatography to afford 0.162 g of (S)-1-[(R)-7-(3,5-dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methyl ester.

The above described methyl ester (0.05 g, 0.08 mmol) was dissolved in THF (2 mL). To this solution was added aqueous 1 N LiOH (0.160 mL) followed by $CH_3OH$ (0.5 mL) and $H_2O$ (0.34 mL). The reaction was stirred for 2 h then diluted with 1 N HCl followed by brine and poured into ethyl acetate. The aqueous phase was separated and extracted twice with ethyl acetate. The organic layers were combined, dried over anhydrous $Na_2SO_4$, decanted and concentrated in vacuo to afford 0.046 g of the title compound (613.1, M+H).

Analogous procedures were employed for the preparation of the following compounds, with 3-azetidinecarboxylic acid being substituted for (S)-(−)-2-azetidinecarboxylic acid.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methyl ester (627.1, M+H).

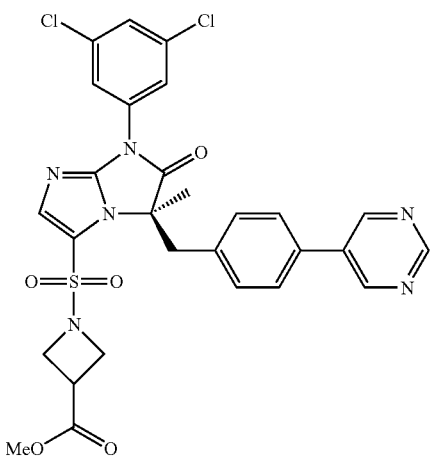

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid (613.1, M+H).

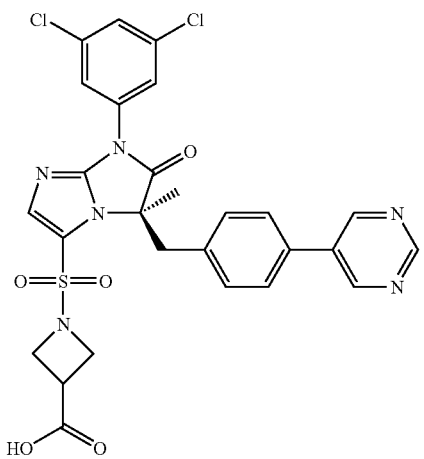

Procedures analogous to those described for Example 1 were employed for the preparation of the following compounds, with the exception that isopropyl alcohol was substituted for methanol in the thionyl chloride-catalyzed esterification step.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid isopropyl ester (655.1, M+H).

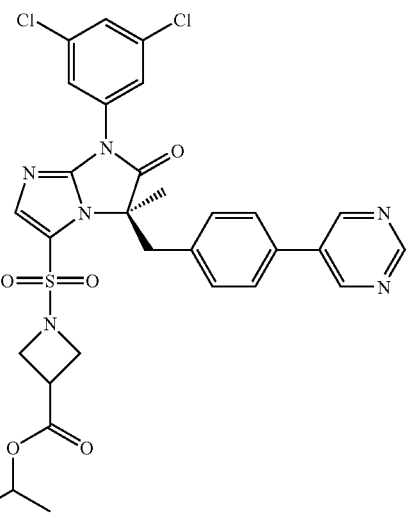

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropyl ester (655.1, M+H).

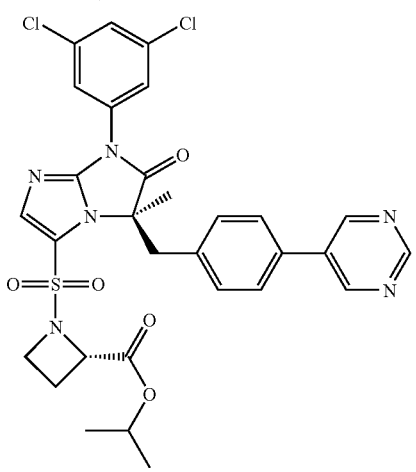

Example 2

Synthesis of (S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropylamide

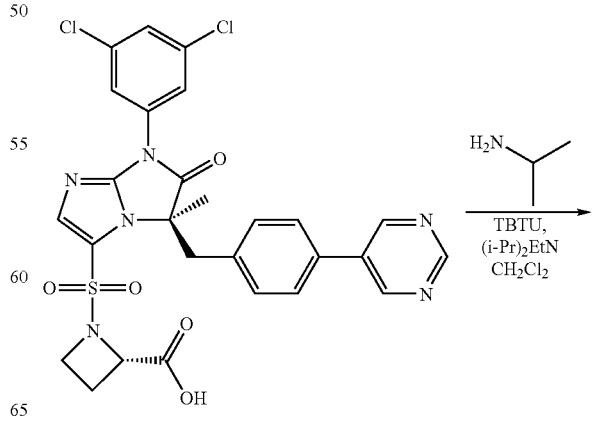

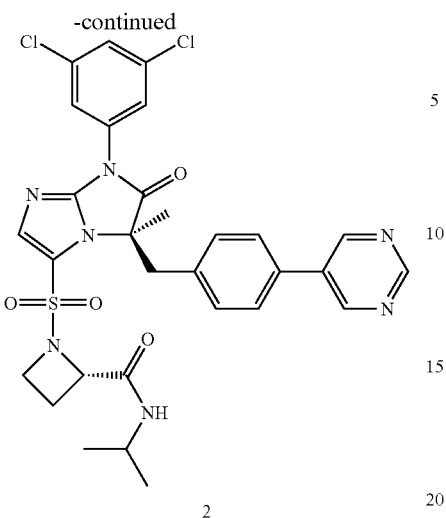

O-Benzotriazol-1-yl-N,N,N',N',-tetramethyluronium tetrafluoroborate (0.016 g), (i-Pr)$_2$EtN (0.013 mL) and (S)-1-[(R)-7-(3,5-dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid (0.023 g, 0.04 mmol) were combined in CH$_2$Cl$_2$ (2 mL) at room temperature. Isopropyl amine (0.0064 mL) was then added and the reaction was stirred for 18 h. The reaction was diluted with CH$_2$Cl$_2$ and poured into saturated aqueous NH$_4$Cl.

The aqueous phase was separated and extracted twice with CH$_2$Cl$_2$. The organic layers were combined, dried over anhydrous Na$_2$SO$_4$, decanted and concentrated in vacuo. The resultant residue was purified by silica gel chromatography to afford 0.008 g of the title compound (654.1, M+H).

Analogous procedures were employed to prepare the following compounds utilizing the corresponding amines as either the free-base, hydrochloride salt or as a commercially available solution.

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methylamide (626.1, M+H).

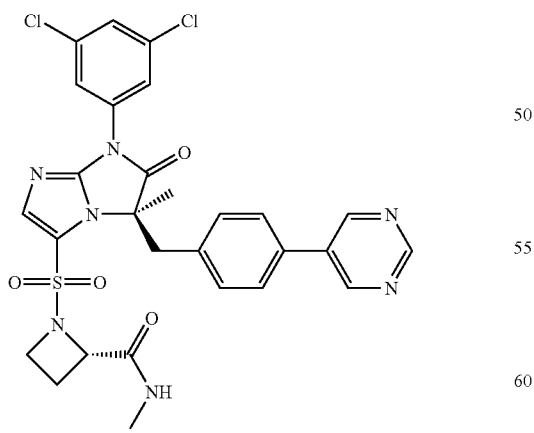

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid dimethylamide (640.1, M+H).

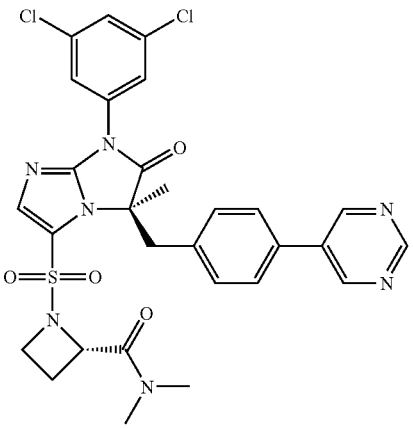

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid benzylamide (702.1, M+H).

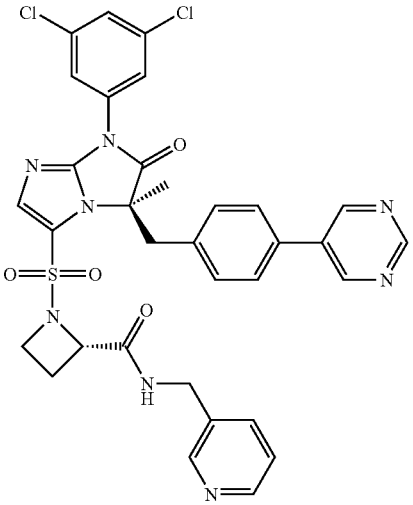

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(3-picoyl)-amide (703.1, M+H).

(R)-1-(3,5-Dichloro-phenyl)-3-methyl-5-[(S)-2-(morpholine-4-carbonyl)-azetidine-1-sulfonyl]-3-(4-pyrimidin-5-yl-benzyl)-1H-imidazo[1,2-α]imidazol-2-one (682.1, M+H).

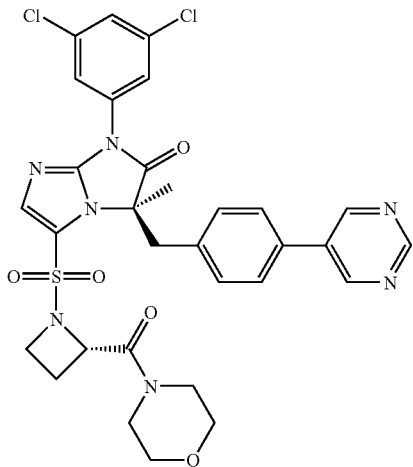

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(2-hydroxy-ethyl)-amide (656.1, M+H).

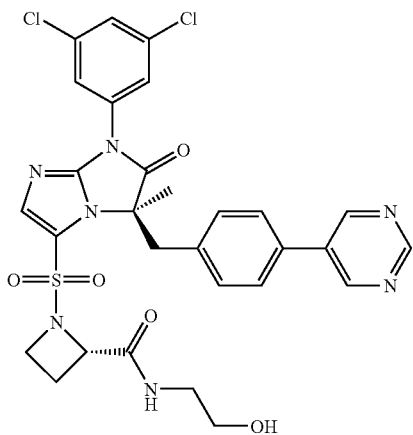

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid((S)-2-hydroxy-1-methyl-ethyl)-amide (670.1, M+H).

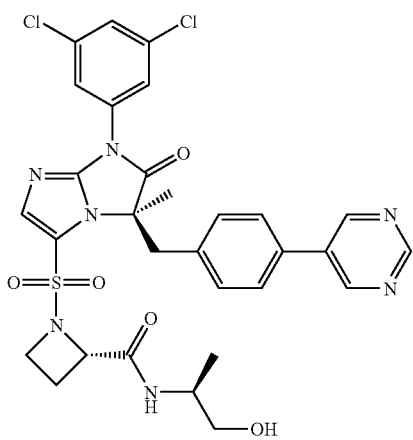

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methylamide (626.1, M+H).

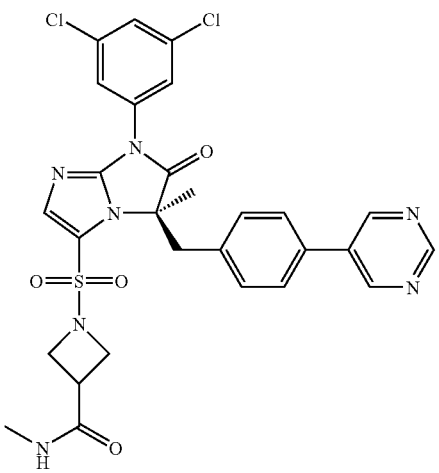

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid dimethylamide (640.1, M+H).

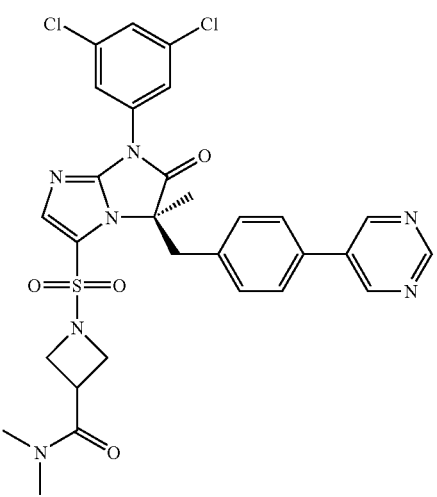

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid isopropylamide (654.1, M+H).

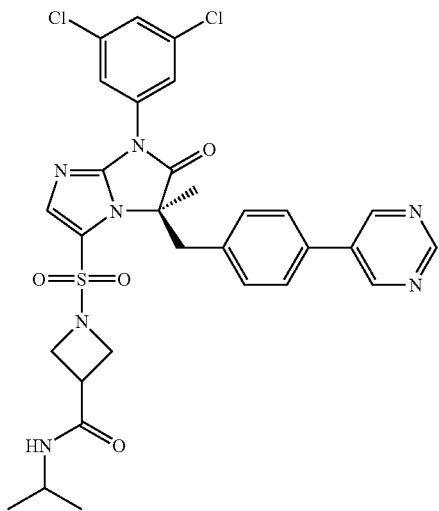

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid benzylamide (702.1, M+H).

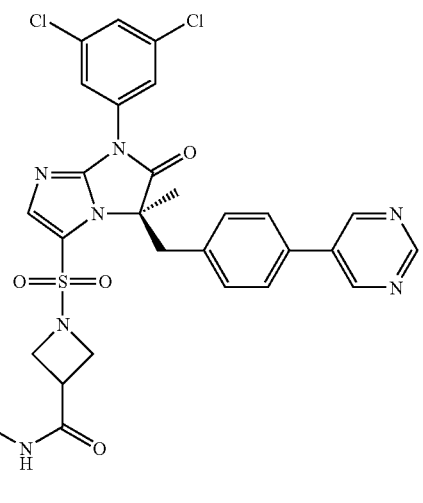

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic (2-hydroxy-ethyl)-amide (656.0, M+H).

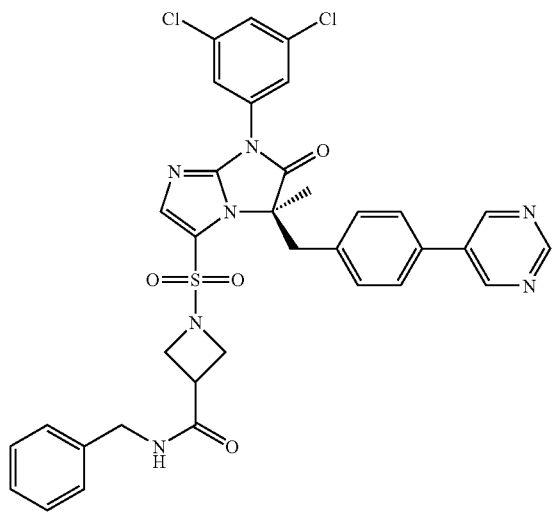

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid(3-picoyl)-amide (703.0, M+H).

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic ((S)-2-hydroxy-1-methyl-ethyl)-amide (669.9, M+H).

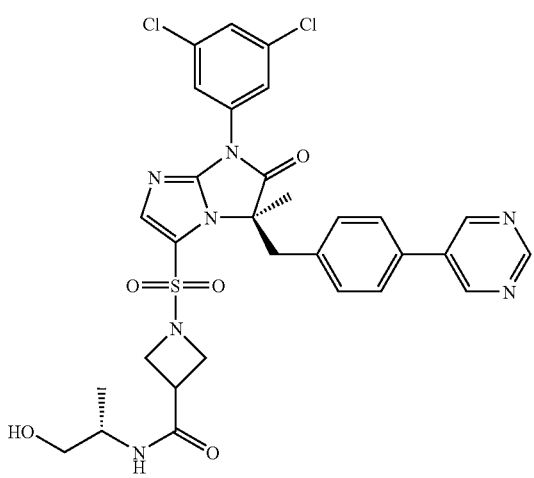

(R)-1-(3,5-Dichloro-phenyl)-3-methyl-5-[3-(morpholine-4-carbonyl)-azetidine-1-sulfonyl]-3-(4-pyrimidin-5-yl-benzyl)-1H-imidazo[1,2-α]imidazol-2-one (682.0, M+H).

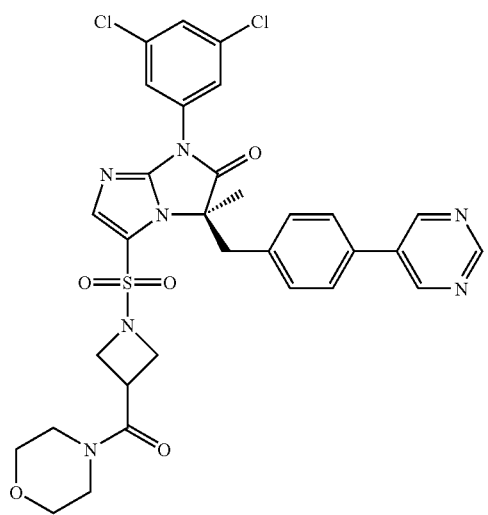

Example 3

Synthesis of (S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid amide

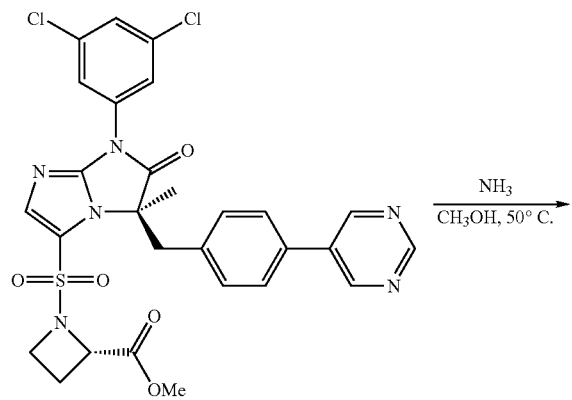

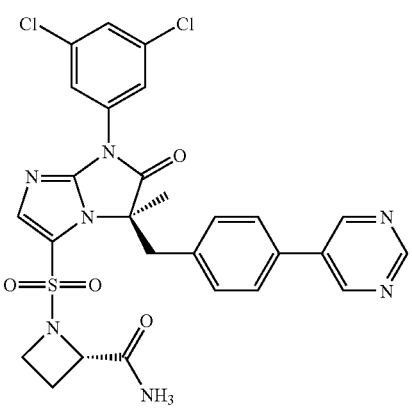

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methyl ester (0.025 g, 0.04 mmol) was dissolved in 2.0 M methanolic ammonia solution (5 mL) in a sealed tube and heated to 50° C. for 48 h. The reaction was cooled to room temperature and the volatiles were removed in vacuo. The resultant residue was purified by silica gel chromatography to afford 0.018 g of the title compound (612.1, M+H).

An analogous procedure was employed for the preparation of the following compound from 1-[(R)-7-(3,5-dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methyl ester.

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid amide (612.1, M+H).

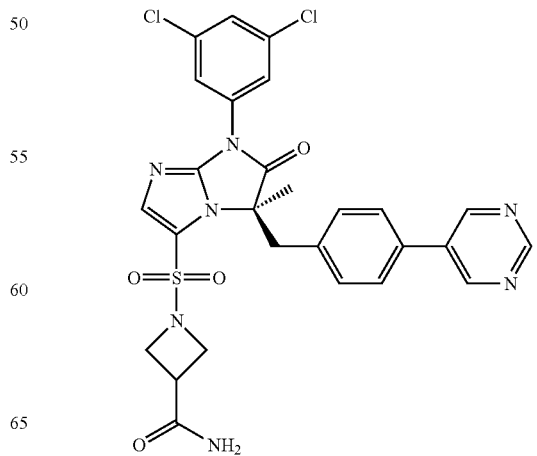

Example 4

Synthesis of (S)-1-[(R)-5-(4-cyano-benzyl)-7-(3,5-dichloro-phenyl)-5-methyl-6-oxo-6,7-dihydro-5H-imidazo[1,2-α]imidazole-3-sulfonyl]-azetidine-2-carboxylic acid amide

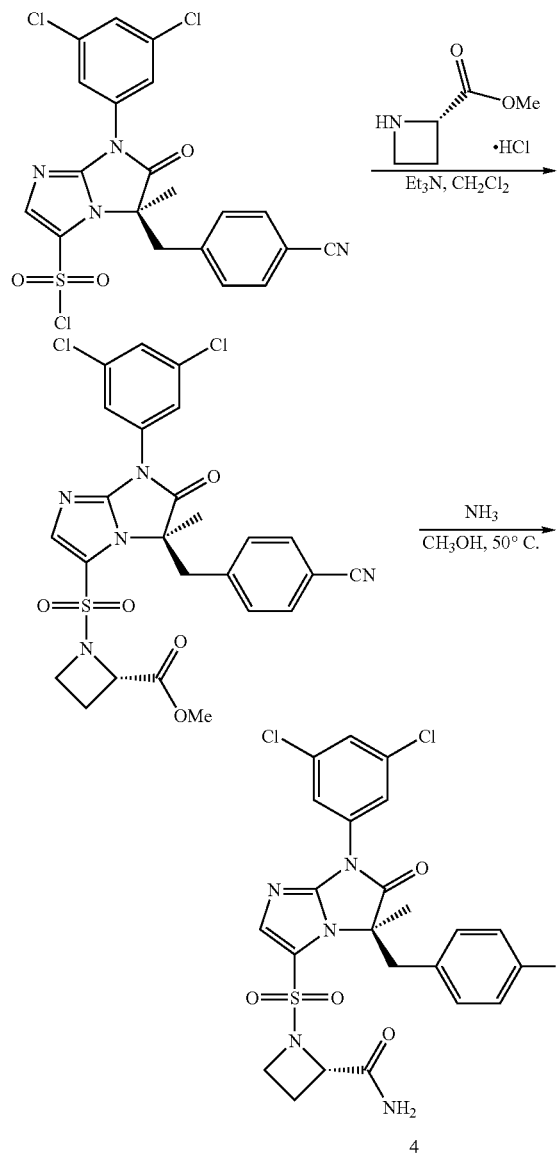

4

(R)-5-(4-Cyano-benzyl)-7-(3,5-dichloro-phenyl)-5-methyl-6-oxo-6,7-dihydro-5H-imidazo[1,2-α]imidazole-3-sulfonyl chloride (0.10 g, 0.2 mmol), as a solution in CH₂Cl₂ (1.0 mL), was added to (S)-(−)-2-azetidinecarboxylic acid methyl ester hydrochloride (0.091 g, 0.6 mmol) in CH₂Cl₂ (1.0 mL). Et₃N (0.084 mL) was added and the reaction was stirred for 18 h at room temperature. The reaction was diluted with CH₂Cl₂ and poured into saturated aqueous NH₄Cl. The aqueous phase was separated and extracted twice with CH₂Cl₂. The organic layers were combined, dried over anhydrous Na₂SO₄, decanted and concentrated in vacuo. The resultant residue was purified by silica gel chromatography to afford 0.08 g of(s)-1-[(R)-5-(4-cyano-benzyl)-7-(3,5-dichloro-phenyl)-5-methyl-6-oxo-6,7-dihydro-5H-imidazo[1,2-α]imidazole-3-sulfonyl]-azetidine-2-carboxylic acid methyl ester.

The above described methyl ester (0.08 g, 0.14 mmol) was dissolved in 2 M methanolic ammonia (5.0 mL) and heated to 50° C. in a sealed tube for 48 h. The reaction was cooled and the volatiles were removed in vacuo. The resultant residue was purified by silica gel chromatography to afford 0.049 g of the title compound (559.4, M+H).

Analogous procedures were employed for the preparation of the following compounds, with (R)-7-(3,5-dichloro-phenyl)-5-methyl-6-oxo-5-(4-trifluoromethoxy-benzyl)-6,7-dihydro-5H-imidazo[1,2-α]imidazole-3-sulfonyl chloride and (R)-5-[4-(4-cyano-pyrimidin-5-yl)-benzyl]-7-(3,5-dichloro-phenyl)-5-methyl-6-oxo-6,7-dihydro-5H-imidazo[1,2-α]imidazole-3-sulfonyl chloride being substituted for (R)-5-(4-cyano-benzyl)-7-(3,5-dichloro-phenyl)-5-methyl-6-oxo-6,7-dihydro-5H-imidazo[1,2-α]imidazole-3-sulfonyl chloride.

(S)-1-[(R)-7-(3,5-dichloro-phenyl)-5-methyl-6-oxo-5-(4-trifluoromethoxy-benzyl)-6,7-dihydro-5H-imidazo[1,2-α] imidazole-3-sulfonyl]-azetidine-2-carboxylic acid amide (618.4, M+H).

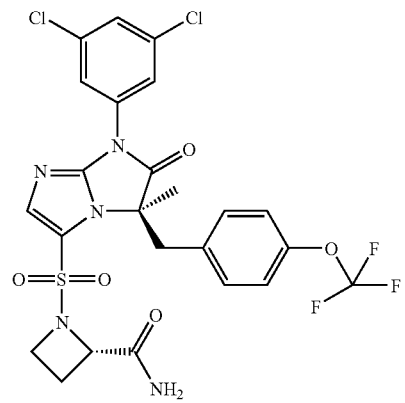

(S)-1-[(R)-5-[4-(4-Cyano-pyrimidin-5-yl)-benzyl]-7-(3,5-dichloro-phenyl)-5-methyl-6-oxo-6,7-dihydro-5H-imidazo[1,2-α]imidazole-3-sulfonyl]-azetidine-2-carboxylic acid amide (637.5, M+H).

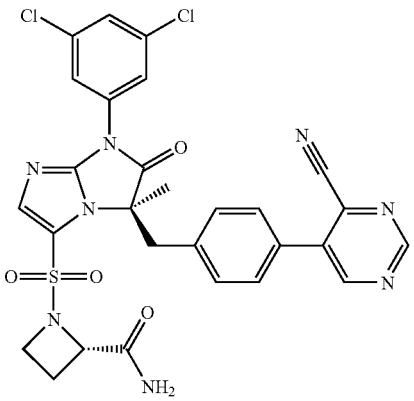

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature,* 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 μg/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d < 10$ μM.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g. as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

Formulations

Compounds of the formula I can be formulated for therapeutic administration in a number of ways. Descriptions of several exemplary formulations are given below.

Example A

| Capsules or Tablets | | | |
|---|---|---|---|
| Example A-1 | | Example A-2 | |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

| Suspension | |
|---|---|
| Ingredients | Quantity |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

| Topical Formulation | |
|---|---|
| Ingredients | Quantity |
| Compound of formula I | 5% by weight |
| Tefose 63 | 13% by weight |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

The invention claimed is:

1. A compound of formula I:

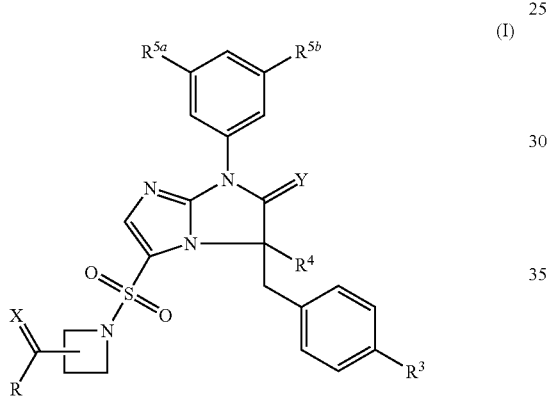

(I)

wherein:

$R$ is $OR^1$ or $NR^1R^2$;

$R^1$ and $R^2$ are each, independently selected from the group consisting of:
(A) hydrogen,
(B) —$R^{100}$, which is:
  a straight or branched alkyl of 1 to 7 carbon atoms or cycloalkyl of 3 to 6 carbon atoms, which alkyl or cycloalkyl group is mono- or poly substituted with moieties independently selected from the group consisting of:
  (i) oxo,
  (ii) cyano,
  (iii) halogen,
  (iv) moieties of the formula —$COOR^6$, wherein $R^6$ is a hydrogen atom, a straight or branched alkyl of 1 to 7 carbon atoms or cycloalkyl of 3 to 6 carbon atoms,
  (v) moieties of the formula —$OR^7$, wherein $R^7$ is a hydrogen atom, a straight or branched alkyl group of 1 to 7 carbon atoms or an acyl group of the formula —$COR^8$ wherein $R^8$ is a straight or branched alkyl group of 1 to 7 carbon atoms,
  (vi) moieties of the formula —$NR^9R^{10}$, wherein $R^9$ and $R^{10}$ are each, independently selected from the group consisting of:
    (a) hydrogen,
    (b) straight or branched alkyl of 1 to 7 carbon atoms,
    (c) acyl of the formula —$COR^{11}$ wherein $R^{11}$ is a straight or branched alkyl group of 1 to 7 carbon atoms, and
    (d) groups of the formula —$COOR^{12}$ wherein $R^{12}$ is a straight or branched alkyl group of 1 to 7 carbon atoms,
  or wherein $R^9$ and $R^{10}$ constitute a bridge consisting of 3-5 methylene groups or 2-4 methylene groups and one oxygen atom, such that the groups $R^9$ and $R^{10}$ together with the nitrogen atom between them form a heterocyclic ring,
  (vii) saturated, heterocyclic groups, consisting of 3 to 5 methylene groups and one oxygen atom, wherein said heterocyclic groups are optionally mono- or disubstituted with moieties that are independently selected from the group consisting of:
    (a) oxo and
    (b) straight or branched alkyl of 1 to 3 carbon atoms; and
  (viii) aryl or heteroaryl selected from the class consisting of:
    (a) phenyl,
    (b) pyridyl,
    (c) furyl,
    (d) tetrazolyl and
    (e) thiophenyl;
(C) aryl, selected from the group consisting of:
  (i) biphenyl,
  (ii) phenyl which is mono- or di-substituted with moieties independently selected from the group consisting of —$NH_2$ and N-morpholino, and
  (iii) quinolinyl; and
(D) unsaturated or partially saturated heterocyclic groups consisting of 2 to 3 carbon atoms, 1 to 2 nitrogen atoms, 0 to 1 sulfur atoms and 0 to 1 oxygen atoms wherein said heterocyclic group is optionally mono- or polysubstituted with one or more of the following moieties independently selected from the group consisting of:
  (i) oxo and
  (ii) straight or branched alkyl of 1 to 7 carbon atoms;
or wherein $R^1$ and $R^2$ constitute a saturated 3 to 5 methylene group bridge which together with the nitrogen atom between them form a heterocyclic ring, wherein one methylene group in the ring may be replaced by O or S, and wherein said heterocyclic ring is mono- or disubstituted with moieties independently selected from the group consisting of:
(A) —OH,
(B) —COOH and
(C) —$COONH_2$;

$R^3$ is:
(A) aryl selected from the group consisting of pyridyl and pyrimidyl, wherein one or more hydrogen atoms of said aryl group are optionally and independently substituted with moieties selected from the group consisting of:
  (i) cyano,
  (ii) halogen and
  (iii) groups of the formula —$NR^{13}R^{14}$, wherein $R^{13}$ and $R^{14}$ are each, independently, hydrogen or straight or branched alkyl of 1 to 3 carbon atoms;
(B) trifluoromethoxy or,
(C) cyano;

R⁴ is straight or branched alkyl of 1 to 3 carbon atoms;
R⁵ᵃ is Cl or CF₃;
R⁵ᵇ is Cl or CF₃;
X is an oxygen or a sulfur atom; and
Y is an oxygen or a sulfur atom;
or a pharmaceutically acceptable salt thereof.

2. A compound of formula I according to claim 1, wherein:
R is OR¹ or NR¹R²,
R¹ and R² are each, independently selected from the group consisting of:
(A) hydrogen
(B) —R¹⁰⁰, which is:
  a straight or branched alkyl of 1 to 4 carbon atoms, which alkyl group is mono- or disubstituted with moieties independently selected from the group consisting of:
  (i) oxo,
  (ii) OH,
  (iii) moieties of the formula —NR⁹R¹⁰, wherein R⁹ and R¹⁰ are each, independently selected from a group consisting of:
    (a) hydrogen and
    (b) methyl,
  (iv) tetrazole,
or wherein R¹ and R² constitute a saturated 5 methylene group bridge which together with the nitrogen atom between them form a heterocyclic ring, wherein said heterocyclic ring is monosubstituted with COOH;
R³ is:
(A) aryl selected from the group consisting of 3-pyridyl and 5-pyrimidyl wherein said aryl group is monosubstituted with:
  (iii) cyano or
  (iv) NH₂,
(B) trifluoromethoxy or
(C) cyano;
R⁴ is a methyl group;
R⁵ᵃ is Cl;
R⁵ᵇ is Cl;
X is an oxygen atom and
Y is an oxygen atom;
or a pharmaceutically acceptable salt thereof.

3. A compound of formula I according to claim 1, wherein:
R is OR¹ or NR¹R²,
R¹ and R² are each, independently selected from the group consisting of:
(A) hydrogen, or
(B) —R¹⁰⁰, which is:
  straight or branched alkyl of 1 to 4 carbon atoms, which alkyl group is mono- or disubstituted with moieties independently selected from the group consisting of:
  (i) oxo,
  (ii) OH and
  (iii) NH₂;
R³ is trifluoromethoxy or cyano;
R⁴ is a methyl group;
R⁵ᵃ is Cl;
R⁵ᵇ is Cl;
X is an oxygen atom; and
Y is an oxygen atom;
or a pharmaceutically acceptable salt thereof.

4. A compound of formula I according to claim 1 having the absolute stereochemistry depicted below by formula I*:

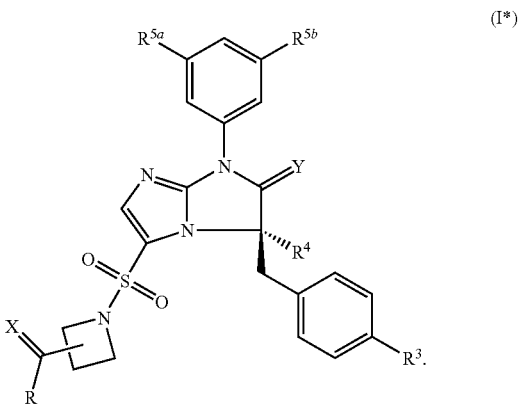

5. A compound of formula (I) according to claim 1, selected from the following:
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methyl ester;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid;
1-[(R)-7-(3,5-Dichloro-phenyl)-5-methyl-6-oxo-5-(4-pyrimidin-5-yl-benzyl)-6,7-dihydro-5H-imidazo[1,2-α] imidazole-3-sulfonyl]-azetidine-3-carboxylic acid methyl ester;
1-[(R)-7-(3,5-Dichloro-phenyl)-5-methyl-6-oxo-5-(4-pyrimidin-5-yl-benzyl)-6,7-dihydro-5H-imidazo[1,2-α] imidazole-3-sulfonyl]-azetidine-3-carboxylic acid;
1-[(R)-7-(3,5-Dichloro-phenyl)-5-methyl-6-oxo-5-(4-pyrimidin-5-yl-benzyl)-6,7-dihydro-5H-imidazo[1,2-α] imidazole-3-sulfonyl]-azetidine-3-carboxylic acid isopropyl ester;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropyl ester;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid isopropylamide;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid methylamide;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid dimethylamide;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid benzylamide;
(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(3-picoyl)-amide;
(R)-1-(3,5-Dichloro-phenyl)-3-methyl-5-[(S)-2-(morpholine-4-carbonyl)-azetidine-1-sulfonyl]-3-(4-pyrimidin-5-yl-benzyl)-1H-imidazo[1,2-α]imidazol-2-one;

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid(2-hydroxy-ethyl)-amide;

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid ((S)-2-hydroxy-1-methyl-ethyl)-amide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid methylamide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid dimethylamide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid isopropylamide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid benzylamide; 1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid(3-picoyl)-amide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic (2-hydroxy-ethyl)-amide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic ((S)-2-hydroxy-1-methyl-ethyl)-amide;

(R)-1-(3,5-Dichloro-phenyl)-3-methyl-5-[3-(morpholine-4-carbonyl)-azetidine-1-sulfonyl]-3-(4-pyrimidin-5-yl-benzyl)-1H-imidazo[1,2-α]imidazol-2-one;

(S)-1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-2-carboxylic acid amide;

1-[(R)-7-(3,5-Dichloro-phenyl)-5-methyl-6-oxo-5-(4-pyrimidin-5-yl-benzyl)-6,7-dihydro-5H-imidazo[1,2-α]imidazole-3-sulfonyl]-azetidine-3-carboxylic acid amide;

(S)-1-[(R)-5-(4-cyano-benzyl)-7-(3,5-dichloro-phenyl)-5-methyl-6-oxo-6,7-dihydro-5H-imidazo[1,2-α]imidazole-3-sulfonyl]-azetidine-2-carboxylic acid amide;

(S)-1-[(R)-7-(3,5-dichloro-phenyl)-5-methyl-6-oxo-5-(4-trifluoromethoxy-benzyl)-6,7-dihydro-5H-imidazo[1,2-α]imidazole-3-sulfonyl]-azetidine-2-carboxylic acid amide;

(S)-1-[(R)-5-[4-(4-Cyano-pyrimidin-5-yl)-benzyl]-7-(3,5-dichloro-phenyl)-5-methyl-6-oxo-6,7-dihydro-5H-imidazo[1,2-α]imidazole-3-sulfonyl]-azetidine-2-carboxylic acid amide;

or a pharmaceutically acceptable salt thereof.

6. A pharmaceutical composition comprising a compound in accordance with claim 1 and at least one pharmaceutically acceptable carrier or adjuvant.

\* \* \* \* \*